(12) United States Patent
Okamoto et al.

(10) Patent No.: US 8,986,195 B2
(45) Date of Patent: Mar. 24, 2015

(54) MEDICAL OPERATION DEVICE

(71) Applicants: Yasuhiro Okamoto, Hachioji (JP); Kazuo Banju, Hachioji (JP)

(72) Inventors: Yasuhiro Okamoto, Hachioji (JP); Kazuo Banju, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 42 days.

(21) Appl. No.: 13/679,176

(22) Filed: Nov. 16, 2012

(65) Prior Publication Data
US 2013/0079595 A1 Mar. 28, 2013

Related U.S. Application Data

(62) Division of application No. 12/119,809, filed on May 13, 2008, now Pat. No. 8,333,689.

(51) Int. Cl.
A61B 1/00 (2006.01)
A61B 5/00 (2006.01)
A61M 25/00 (2006.01)
A61B 1/04 (2006.01)
(Continued)

(52) U.S. Cl.
CPC .............. *A61B 1/01* (2013.01); *A61B 1/00142* (2013.01); *A61B 1/00147* (2013.01); *A61B 1/0052* (2013.01); *A61B 1/0016* (2013.01)
USPC ........... 600/102; 600/104; 600/106; 600/114; 600/115; 600/116; 600/434; 600/585

(58) Field of Classification Search
USPC ......... 600/102, 104, 106, 118, 131, 146, 101, 600/107, 121–125, 585, 114–116, 127, 129, 600/153, 154, 434; 604/165.04, 159, 604/164.13, 434, 510, 528, 96.01
See application file for complete search history.

(56) References Cited

U.S. PATENT DOCUMENTS

| 4,610,242 A | 9/1986 | Santangelo et al. ............... 128/4 |
| 4,741,326 A * | 5/1988 | Sidall et al. .................... 600/123 |
| 5,855,569 A * | 1/1999 | Komi ............................ 604/526 |

(Continued)

FOREIGN PATENT DOCUMENTS

| EP | 1 582 139 A2 | 10/2005 |
| EP | 1 987 788 A1 | 11/2008 |

(Continued)

*Primary Examiner* — Ryan Henderson
(74) *Attorney, Agent, or Firm* — Scully, Scott, Murphy & Presser, PC

(57) ABSTRACT

A medical operation device is attachable to an insertion portion of a medical instrument for observation. The medical operation device includes: rotary cylinder rotatably disposed in device main body that has insertion portion inserting hole through which insertion portion is inserted; insertion portion pressing member that presses insertion portion inside rotary cylinder; insertion portion mounting section cover provided inside insertion portion inserting hole that prevents insertion portion directly touching inner face of insertion portion inserting hole, vicinity of opening of insertion portion inserting hole, and insertion portion pressing member; switching instruction portion that switches whether insertion portion pressing member presses insertion portion to specify state where rotary cylinder and insertion portion are united and state where insertion portion moves forward/rearward with respect to rotary cylinder; and rotation mechanism that, when rotary cylinder and insertion portion are united, rotates rotary cylinder to rotate insertion portion unified with rotary cylinder around insertion portion axis.

1 Claim, 13 Drawing Sheets

(51) Int. Cl.
*A61B 1/01* (2006.01)
*A61B 1/005* (2006.01)

(56) References Cited

U.S. PATENT DOCUMENTS

| | | |
|---|---|---|
| 6,981,945 B1 | 1/2006 | Sarvazyan et al. ............ 600/131 |
| 2001/0056220 A1 | 12/2001 | Fujikura et al. ............... 600/118 |
| 2002/0103418 A1 | 8/2002 | Maeda et al. ................. 600/132 |
| 2003/0212308 A1 | 11/2003 | Bendall ......................... 600/131 |
| 2005/0228228 A1 | 10/2005 | Boulais ......................... 600/131 |
| 2006/0058579 A1 | 3/2006 | Oberlaender et al. ........ 600/102 |
| 2007/0100201 A1 | 5/2007 | Komiya et al. ............... 600/118 |
| 2007/0191674 A1 | 8/2007 | Zirps et al. .................... 600/104 |
| 2007/0265497 A1 | 11/2007 | Brown et al. ................. 600/114 |
| 2008/0287739 A1 | 11/2008 | Smith et al. .................. 600/131 |
| 2009/0156897 A1 | 6/2009 | Omot et al. ................... 600/118 |

FOREIGN PATENT DOCUMENTS

| | | |
|---|---|---|
| JP | 2003-140055 | 5/2003 |
| JP | 2006/198299 | 8/2006 |
| JP | 2007-125180 | 5/2007 |
| WO | 2007/043118 A1 | 4/2007 |
| WO | 2007/096950 A1 | 8/2007 |

\* cited by examiner

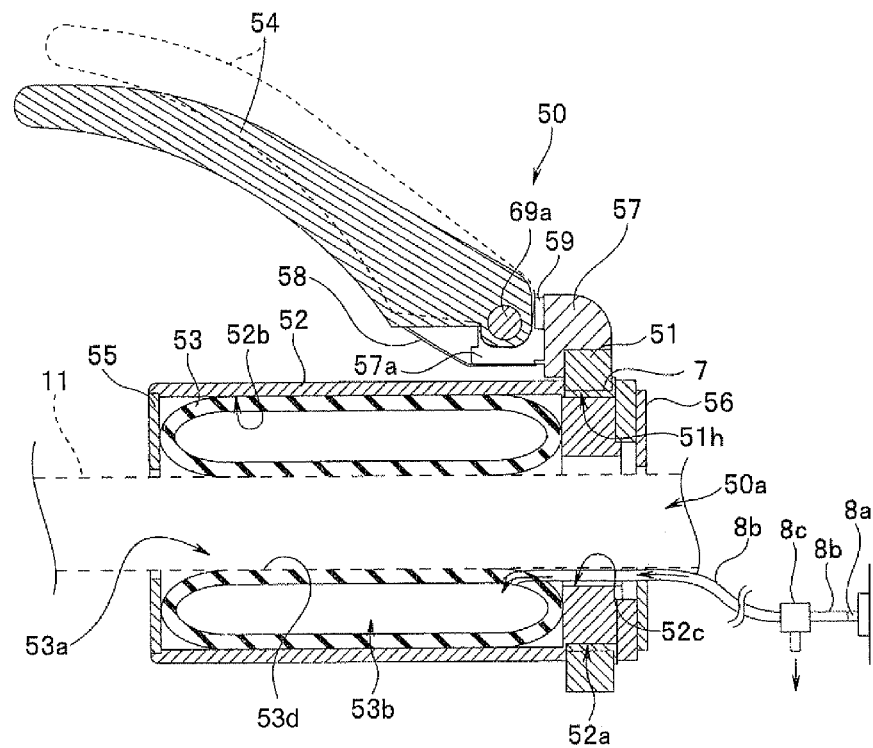
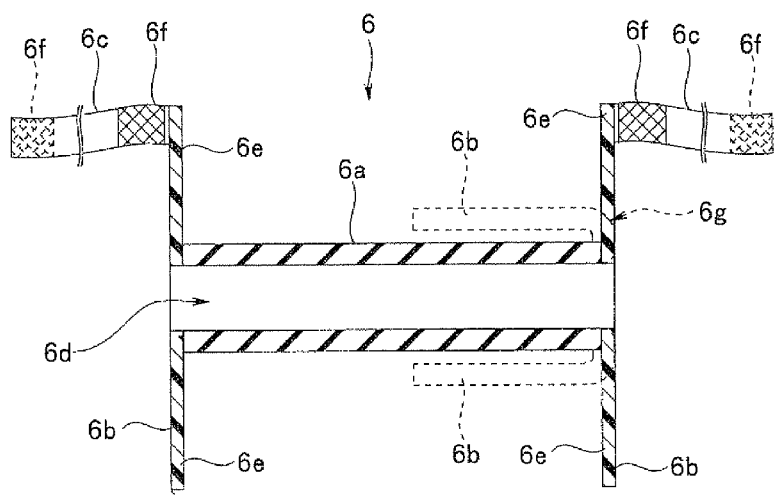

MEDICAL OPERATION DEVICE

CROSS-REFERENCE TO RELATED APPLICATION

This application is a Divisional Application of U.S. application Ser. No. 12/119,809 filed on May 13, 2008, the entire contents of which are incorporated herein by reference.

BACKGROUND OF THE INVENTION

1. Field of the Invention

The present invention relates to a medical operation device that is attached to an insertion portion of a medical instrument for observation and that has excellent workability and operability.

2. Description of the Related Art

In recent years, medical endoscopes have been used which perform observation of a diseased part or the like inside a body by inserting a long and narrow insertion portion into the body and which, as necessary, can perform various kinds of therapeutic treatment using a treatment instrument that is passed through the inside of a treatment instrument channel.

In this kind of endoscope, to improve the insertability to a curved site and to enable an observation optical system or the like that is provided at a distal end portion to be directed in a desired direction, for example, a bending portion that bends vertically and laterally is provided at the distal end side of the insertion portion. Further, when introducing the insertion portion into a target site within the body, in addition to performing an operation that bends the bending portion, a surgeon also performs an operation that twists the insertion portion.

For example, U.S. Patent Application Publication No. 2007-0100201A1 discloses an endoscope system in which, while grasping the insertion portion of an endoscope, the surgeon can easily execute various functions of a treatment instrument that is inserted through a treatment instrument channel of the endoscope or various functions of the endoscope. In this endoscope system, an operation instructing device is disclosed that allows a surgeon to operate a bending knob with a hand that grasps the operation portion of the endoscope, and in addition to operating the insertion portion with the hand that grasps the insertion portion, the surgeon can also operate the various respective functions of the endoscope and a treatment instrument with that hand. Further, in this endoscope system, the operation instructing device is united with the insertion portion by operating a fixed lever.

Furthermore, Japanese Patent Application Laid-Open Publication No. 2003-140055 discloses an endoscope apparatus in which holding of an insertion portion can be easily and securely performed with a hand that grasps an operation portion or a remote control. In this endoscope apparatus, an insertion portion is passed through an insertion portion inserting section of an insertion portion holding tool and a remote control is provided at a mounting portion. In this state, by strengthening or relaxing a force that grasps the insertion portion holding tool, the surgeon can easily switch between a state in which the insertion portion is fixed to the remote control and a state in which the insertion portion can freely move forward or backward with respect to the remote control. A bending lever comprising a bending operation switch that the surgeon operates when bending a bending portion of the insertion portion is provided in the remote control of the endoscope apparatus. Thus, the surgeon can perform an operation that bends the bending portion with the hand that grasps the insertion portion.

Thus, according to the above described operation instructing device, it is possible for the surgeon to release a hand from the operation instructing device. In contrast, although it is not possible for the surgeon to release a hand from the insertion portion holding tool, a fixed state and a state of forward/rearward movement are easily obtainable. However, the above described operation instructing device and insertion portion holding tool are provided directly on the insertion portion. Therefore, with respect to the operation instructing device or the insertion portion holding tool, it is necessary to enable a fixed state or a state of forward/rearward movement to be easily obtainable in a condition in which the surgeon can release their hands, and also to prevent adherence of body fluid or dirt that adheres to the insertion portion at a mounting section with the insertion portion.

SUMMARY OF THE INVENTION

A medical operation device of the present invention is a medical operation device that is attachable to an insertion portion of a medical instrument for observation. The medical operation device includes a rotary cylinder, an insertion portion pressing member, an insertion portion mounting section cover, a switching instruction portion, and a rotation mechanism. The rotary cylinder is rotatably provided on the device main body. The rotary cylinder includes an insertion portion inserting hole through which the insertion portion is inserted. The insertion portion pressing member presses the insertion portion that is disposed inside the rotary cylinder. The insertion portion mounting section cover is arranged inside the insertion portion inserting hole and prevents the insertion portion directly touching an inner face of the insertion portion inserting hole, the insertion portion directly touching the vicinity of an opening of the insertion portion inserting hole, and the insertion portion directly touching the insertion portion pressing member. The switching instruction portion switches whether or not the insertion portion pressing member presses the insertion portion. The switching instruction portion issues an instruction to enter a state in which the rotary cylinder and the insertion portion are united, and a state in which the insertion portion moves forward/rearward with respect to the rotary cylinder. The rotation mechanism rotates the rotary cylinder when the rotary cylinder and the insertion portion are united to cause the insertion portion that is united with the rotary cylinder to rotate around the axis of the insertion portion.

The above and other objects, features and advantages of the invention will become more clearly understood from the following description referring to the accompanying drawings.

BRIEF DESCRIPTION OF THE DRAWINGS

FIG. 4 is a sectional view illustrating the configuration inside a rotary cylinder of the electric bending operation device;

FIG. 5 is a view illustrating the configuration of an insertion portion mounting section cover;

DETAILED DESCRIPTION OF THE PREFERRED EMBODIMENTS

Hereunder, embodiments of the present invention are described with reference to the drawings.

The first embodiment is described below referring to FIG. 1 to FIG. 6.

Figure 1:
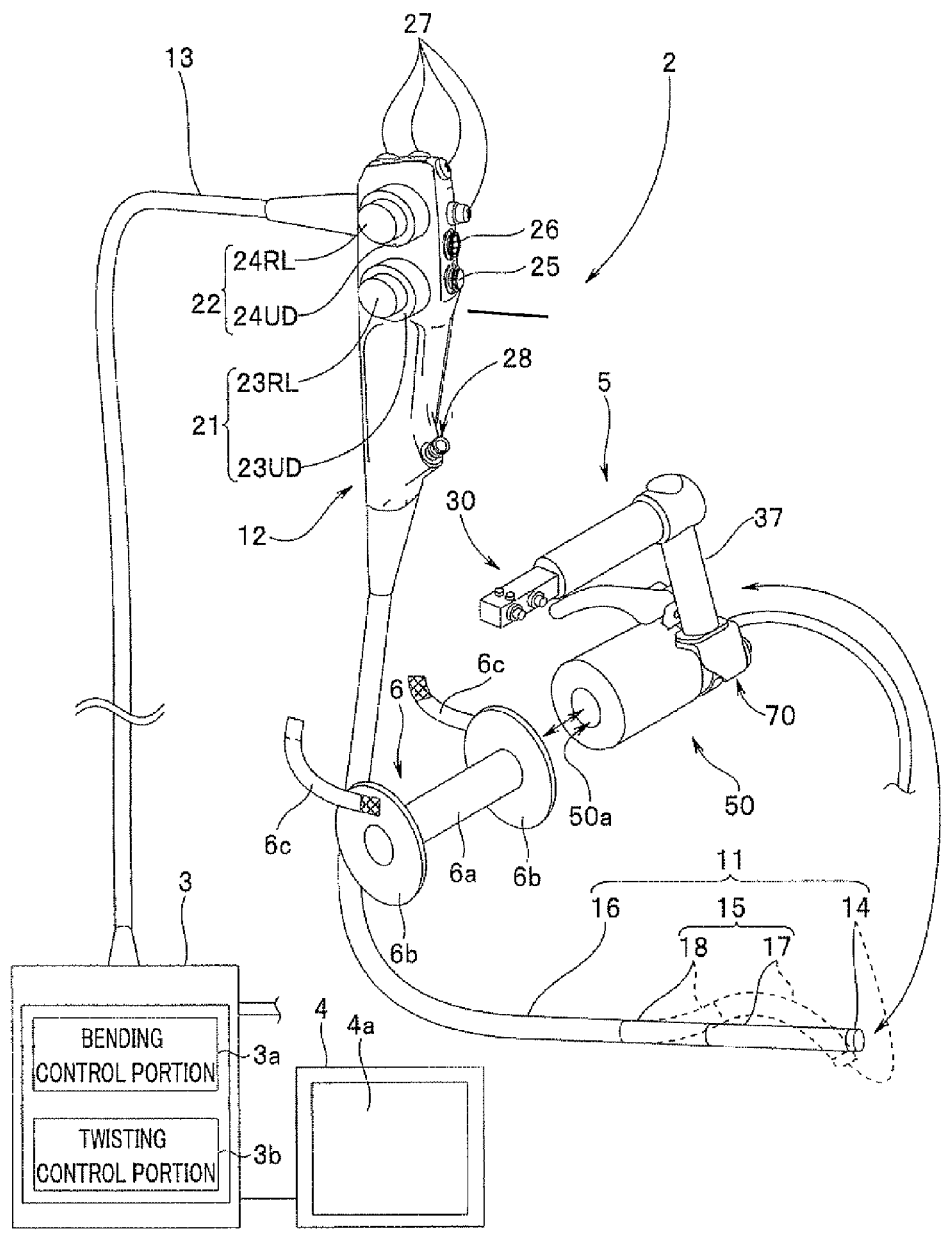
FIG. 1 is a view that illustrates an endoscope system.

As shown in FIG. 1, an endoscope system 1 of the present embodiment includes an electric bending endoscope 2, an endoscope control device 3, a display device 4, an electric bending operation device 5 that is an operation device, and an insertion portion mounting section cover (hereunder, abbreviated as "cover") 6.

The electric bending endoscope 2 is a medical instrument for observation, and includes an insertion portion 11 that is inserted inside the body, an operation portion 12 that is provided on the proximal end side of the insertion portion 11, and a universal cord 13 that extends from the operation portion 12. The proximal end portion of the universal cord 13 is connected to the endoscope control device 3. The endoscope control device 3 is provided with an illumination portion, an image processing portion, control portions 3a and 3b, and the like. The illumination portion includes a power supply portion that supplies power to a light emitting device such as an LED or an illumination lamp that emits an illuminating light from an illumination window of a distal end portion 14, described later, of the electric bending endoscope 2. The image processing portion includes a drive circuit that drives a solid-state image pickup device such as a CCD or a CMOS that is housed in the distal end portion, and an image processing circuit that generates video signals from image signals that are generated by photoelectric conversion at the solid-state image pickup device and transmitted to the image processing circuit. Video signals that are generated at the image processing circuit of the image processing portion are outputted to the display device 4 and displayed as endoscopic images on a screen 4a.

The insertion portion 11 is configured by the distal end portion 14, an electric bending portion 15, and a flexible tube portion 16 that are provided in a linked manner in this order from the distal end side. The electric bending portion 15 of the present embodiment, for example, includes a first bending portion 17 and a second bending portion 18. The first bending portion 17 and the second bending portion 18 include a plurality of bending pieces (not shown) that are rotatably connected in a predetermined direction and bend vertically and laterally. Distal end portions of angle wires for the top, bottom, left and right are respectively provided in a fixed condition at positions corresponding to the top, bottom, left and right of a tip piece (not shown) that is positioned at the extreme tip of each of the bending portions 17 and 18.

According to the present embodiment, the electric bending portion 15 includes the first bending portion 17 and the second bending portion 18 that bend the electric bending portion 15 vertically and laterally. However, the electric bending portion 15 is not limited to this configuration, and a configuration may be adopted that includes only the first bending portion 17, or in which the second bending portion 18 bends vertically, or which includes bending portion that bends vertically and laterally or bends vertically as a third bending portion.

On one side surface or another side surface of the operation portion 12 are arranged a first bending portion operation section 21 and a second bending portion operation section 22. The first bending portion operation section 21 includes, for example, a first vertically bending knob 23UD and a first laterally bending knob 23RL that are rotatably provided on the same axis. The second bending portion operation section 22 includes a second vertically bending knob 24UD and a second laterally bending knob 24RL that are rotatably provided on the same axis.

The bending portions 17 and 18 are bent, for example, downward by rotating the vertical knobs 23UD and 24UD clockwise as viewed from the position of the surgeon. Further, the bending portions 17 and 18 are bent, for example, upward by rotating the vertical knobs 23UD and 24UD counter-clockwise. Meanwhile, when the lateral knobs 23RL and 24RL are rotated clockwise, the bending portions 17 and 18 bend to the right, and when the lateral knobs 23RL and 24RL are rotated counter-clockwise, the bending portions 17 bend to the left.

On a longitudinal side surface 19 that is sandwiched between one side surface and the other side surface are provided an air/water supply button 25, a suction button 26, and a plurality of buttons 27 for performing various operations such as switching the display of the display device 4 or issuing an instruction to freeze or release a display image. Further, a treatment instrument insertion opening 28 for introducing a treatment instrument into a treatment instrument channel is provided in the operation portion 12.

Inside the operation portion 12 of the electric bending endoscope 2 are provided, for example, a first vertically bending motor (not shown), a first laterally bending motor (not shown), a second vertically bending motor (not shown), and a second laterally bending motor (not shown). The first vertically bending motor pulls and slackens an up angle wire and a down angle wire of the first bending portion 17. The first laterally bending motor pulls and slackens a left angle wire and a right angle wire of the first bending portion 17. The second vertically bending motor, meanwhile, pulls and slackens an up angle wire and a down angle wire of the second bending portion 18. The second laterally bending motor pulls and slackens a left angle wire and a right angle wire of the second bending portion 18.

Inside the operation portion 12 is provided an unshown knob encoder that detects a rotation amount and a rotation direction, respectively, of the knobs 23UD, 23RL, 24UD, and 24RL. When any of the knobs 23UD, 23RL, 24UD, and 24RL is rotated clockwise or counter-clockwise by a surgeon or the like, the knob encoder outputs a knob rotation control signal that indicates the rotation direction and the rotation amount of the respective knobs to a bending control portion 3a that is a first drive control portion of the endoscope control device 3.

Simultaneously with the input of a rotation control signal, the bending control portion 3a calculates the pulling amount of an angle wire by a wire drive motor that corresponds to the rotation control signal, and outputs a bending control signal to the corresponding wire drive motor. Thereupon, the wire drive motor corresponding to the knob operation performed by the surgeon is driven and the electric bending portion 15 performs a bending operation as illustrated, for example, by the dashed lines.

The electric bending operation device 5 is mounted to the insertion portion 11 of the electric bending endoscope 2 for use. The insertion portion 11 is inserted through an insertion portion inserting hole 50a of the electric bending operation device 5. The electric bending operation device 5 principally includes an insertion portion operation section 30 and an insertion portion mounting mechanism 50. A rotation mechanism 70 is arranged in the insertion portion mounting mechanism 50. Reference numeral 37 denotes a support column that unites the insertion portion operation section 30 and the insertion portion mounting mechanism 50.

The cover 6 includes a covering portion for an inner face of an inserting hole (hereunder, abbreviated as "hole covering portion") 6a, rotary portion side surface covering portions (hereunder, abbreviated as "side surface covering portions") 6b, and a fixing portion 6c. The cover 6 prevents body fluid or the like that adheres to the insertion portion 11 that is inserted inside the body from adhering to the insertion portion mounting mechanism 50 of the electric bending operation device 5.

The insertion portion operation section 30 will now be described referring to FIG. 2, FIG. 3, and FIG. 4.

Figure 2:
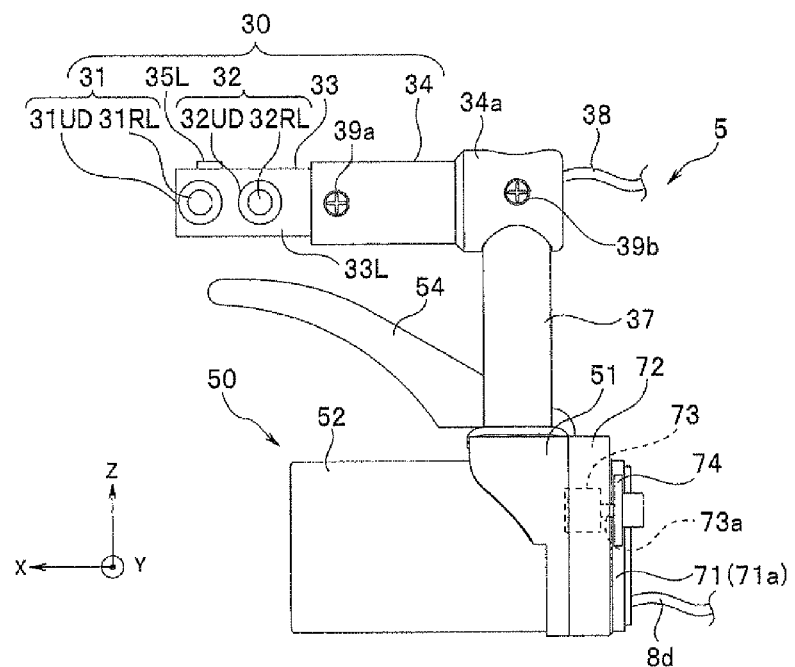
FIG. 2 is a side surface view of an electric bending operation device as a medical operation device.
Figure 3:
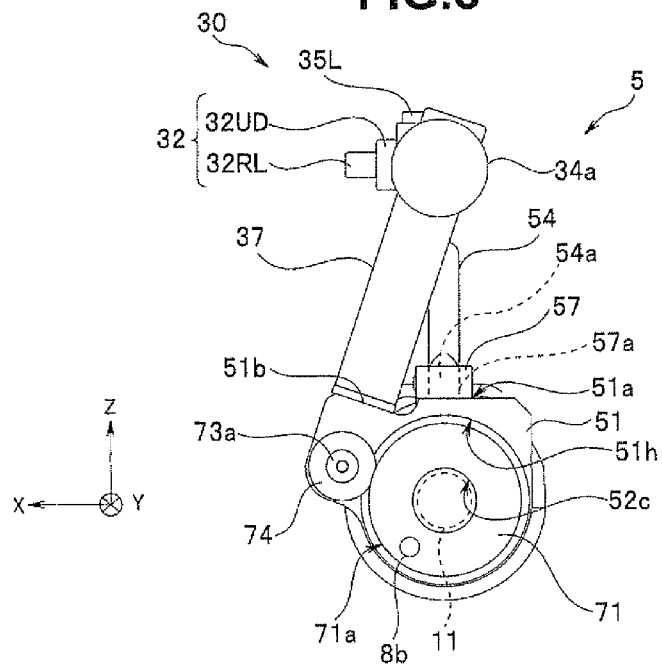
FIG. 3 is a rear view of the electric bending operation device.

In the present embodiment, a direction indicated by an arrow X in FIGS. 2 and 3 is taken as the distal end direction and the opposite direction thereto is taken as the proximal end direction. Further, a direction indicated by an arrow Y is taken as the left direction and the opposite direction thereto is taken as the right direction. Furthermore, a direction indicated by an arrow Z is taken as the upward direction and the opposite direction thereto is taken as the downward direction.

As shown in FIGS. 2 to 4, the insertion portion operation section 30 includes a first knob portion 31, a second knob portion 32, and twisting operation buttons 35. According to the present embodiment, the insertion portion operation section 30 is attached to an operation portion support member 34 via a fixed rod 33.

The first knob portion 31 corresponding to the first bending portion operation section 21 provided in the operation portion 12 of the electric bending endoscope 2, and the second knob portion 32 corresponding to the second bending portion operation section 22 are arranged, for example, in the X direction on a left side surface 33L of the fixed rod 33.

The twisting operation buttons 35 include a button 35L and an unshown button 35R that indicate a twisting direction. The buttons 35L and 35R are arranged, for example, in the Y direction on the top surface of the fixed rod 33.

The first knob portion 31 includes a first vertically bending knob 31UD and a first laterally bending knob 31RL that have the similar functions as the first vertically bending knob 23UD and the first laterally bending knob 23RL. The second knob portion 32 includes a second vertically bending knob 32UD and a second laterally bending knob 32RL that have the similar functions as the second vertically bending knob 24UD and the second laterally bending knob 24RL.

Inside the fixed rod 33 is provided an unshown knob encoder that detects a rotation amount and a rotation direction, respectively, of the knobs 31UD, 31RL, 32UD, and 32RL. When any of the knobs 31UD, 31RL, 32UD, and 32RL is rotated clockwise or counter-clockwise by a surgeon or the like, the knob encoder outputs a knob rotation control signal that indicates the rotation direction and the rotation amount of the respective knobs to the bending control portion 3a that is the first drive control portion of the endoscope control device 3.

Simultaneously with the input of a rotation control signal from any of the knobs 31UD, 31RL, 32UD, and 32RL, the bending control portion 3a calculates the pulling amount of an angle wire by a wire drive motor that corresponds to the rotation control signal, and outputs a bending control signal to the corresponding wire drive motor. Thereupon, the wire drive motor corresponding to the knob operation is driven such that the electric bending portion 15 performs a bending operation.

The buttons 35L and 35R indicate the rotation direction and rotation amount of an insertion portion rotation motor (denoted by reference numeral 73 in FIG. 3 as described later). While the button 35R or 35L is being pressed down, a twisting control signal is outputted to the twisting control portion 3b that is a second drive control portion of the endoscope control device 3. The button 35L outputs a twisting control signal that rotates the insertion portion 11 in the leftward direction, and the button 35R outputs a twisting control signal that rotates the insertion portion 11 in the rightward direction.

Simultaneously to the input of a twisting control signal, the twisting control portion 3b outputs a twisting operation signal that actuates the insertion portion rotation motor.

The fixed rod 33 is integrally fixed to the distal end side of the operation portion support member 34 by, for example, a screw 39a. The operation portion support member 34 also serves as a grasping portion, and a proximal end portion 34a thereof is integrally fixed to the support column 37 by, for example, a screw 39b. The longitudinal axis of the operation portion support member 34 and the X axis of the electric bending operation device 5 are set in a parallel relationship.

Note that, signal wires that extend from the twisting operation buttons 35, the first knob portion 31, and the second knob portion 32, respectively, are passed through the inside of a protective tube 38 that extends from the proximal end portion 34a of the operation portion support member 34 and connected to the endoscope control device 3.

Next, the insertion portion mounting mechanism 50 that includes the rotation mechanism 70 is described referring to FIG. 2 to FIG. 4.

First, the insertion portion mounting mechanism 50 is described.

As shown in FIG. 2 to FIG. 4, the insertion portion mounting mechanism 50 principally includes a rotation holding portion 51, a rotary cylinder 52 that also serves as the rotation mechanism 70, an insertion portion mounting section cover 6, an air bag 53, and a lever 54. Reference numerals 55 and 56 denote lids. The lids 55 and 56 include openings 55o and 56o that forms the insertion portion inserting hole 50a. The lids 55 and 56 are fixed to the rotary cylinder 52, and forms the distal end face and proximal end face of the rotary cylinder 52, respectively.

The rotation holding portion 51 is the device main body, and includes a through-hole 51h as shown in FIG. 4. A bearing 7 is provided inside the through-hole 51h. A rotary portion 52a of the rotary cylinder 52 is rotatably retained by the bearing 7.

As shown in FIG. 3, a lever mounting portion 51a and a support column mounting portion 51b are provided in the rotation holding portion 51. A lever supporting member 57 is fixed by screwing in the lever mounting portion 51a.

As shown in FIG. 3 and FIG. 4, the lever supporting member 57 includes a pair of supporting portions 57a that are vertically arranged. A fulcrum portion 54a of the lever 54 is disposed between the supporting portions 57a. The fulcrum portion 54a is rotatably attached to the supporting portions 57a by a first pin 69a. As a result, the lever 54 moves from a position indicated by a solid line to a position indicated by a dashed line as a switching instruction portion.

Reference numeral 58 denotes a plate spring. The lever 54 is disposed at the position indicated by the solid line by the urging force of the plate spring 58. Reference numeral 59 denotes, for example, a proximity switch. When the lever 54 that is the switching instruction portion is disposed at the position indicated by the dashed line against the urging force of the plate spring 58, the proximity switch 59 outputs an "on" signal to the endoscope control device 3. Upon input of the output signal from the proximity switch 59, the endoscope control device 3 switches an electromagnetic valve 8c, described later, from a gas supply state to an atmosphere release state. Thereafter, when the lever 54 is moved to the position indicated by the solid line by the urging force of the plate spring 58, the proximity switch 59 is switched to an "off" state. Thereupon, the electromagnetic valve 8c is again switched to a gas supply state.

The rotary cylinder 52 includes a hollow portion 52b and an insertion portion introduction hole 52c. The insertion portion introduction hole 52c is a through-hole that forms the insertion portion inserting hole 50a, and links the hollow portion 52b and the outside. In the present embodiment, the hollow portion 52b is an air bag installation hole.

The air bag 53 is made with an elastic member such as rubber. The air bag 53 includes a mounting/demounting hole 53a. The air bag 53 is a tube element that is formed in a so-called pipe shape. At a solid portion of the pipe shape is provided a fluid chamber 53b that comprises a single space so as to cover the circumference of the mounting/demounting hole 53a.

An unshown mouthpiece with a check valve is connected to the fluid chamber 53b. The inside of the fluid chamber 53b is normally set to a forward/rearward movement enabling pressure that is a pressure at which the insertion portion 11 can smoothly move forward and rearward inside the mounting/demounting hole 53a. When the pressure of the fluid chamber 53b is the forward/rearward movement enabling pressure, the mounting/demounting hole 53a functions as the insertion portion inserting hole 50a.

Nitrogen gas, for example, is supplied to the fluid chamber 53b via a supply tube 8b that links, for example, a supply port 8a provided on a wall of an operating room and a connection mouthpiece. The electromagnetic valve 8c is arranged partway along the supply tube 8b. The electromagnetic valve 8c is configured to be capable of switching between a gas supply state that supplies nitrogen gas to the fluid chamber 53b and an atmosphere release state in which nitrogen gas of the fluid chamber 53b is released to the atmosphere.

The air bag 53 is expanded by nitrogen gas being supplied into the fluid chamber 53b of the air bag 53. As the air bag 53 is expanded in a state in which the air bag 53 is housed inside the hollow portion 52b, the hole diameter of the mounting/demounting hole 53a gradually becomes smaller.

Figure 6:
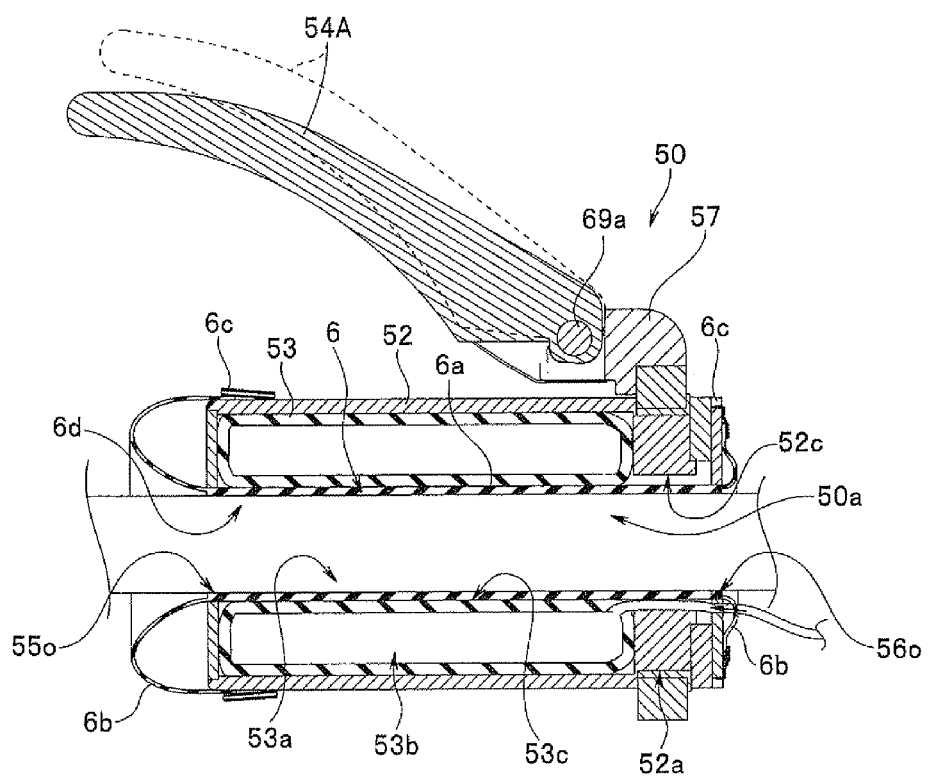
FIG. 6 is a view illustrating a state in which an electric bending operation device and an insertion portion that is inserted through an insertion portion inserting hole of the electric bending operation device are integrally fixed together.

When the insertion portion 11 is inserted into the mounting/demounting hole 53a while the air bag 53 is in an expanded state, the amount of a pressing force that presses the insertion portion 11 gradually increases along with the expansion of the air bag 53. The pressure inside the fluid chamber 53b then reaches a fixing pressure that places the insertion portion 11 and the electric bending operation device 5 in a state in which they are integrally fixed to each other and, as shown in FIG. 6, the air bag 53 enters a state in which the air bag 53 is in intimate contact with the inner face of the hollow portion 52b and the insertion portion 11. At this time, the insertion portion 11 and the rotary cylinder 52 provided with the air bag 53 enter a state in which they are integrally fixed together.

Note that, the pressure inside the fluid chamber 53b is monitored via an unshown pressure gauge that is provided partway along the supply tube 8b. The endoscope control device 3 controls the supply of nitrogen gas based on a detection signal that is outputted from the pressure gauge. When the endoscope control device 3 confirms that an "on" signal is outputted from the proximity switch 59 upon the lever 54 being operated, the endoscope control device 3 switches the electromagnetic valve 8c to an atmosphere release state. Thereupon, nitrogen gas inside the fluid chamber 53b is released into the atmosphere by the elastic force of the air bag 53 to decrease the pressure of the fluid chamber 53b to the forward/rearward movement enabling pressure. Meanwhile, when the lever 54 is returned to the solid line position from the dashed line position, the output of an "on" signal from the proximity switch 59 stops. Thereupon, the endoscope control device 3 switches the electromagnetic valve 8c to a gas supply state again. As a result, the pressure inside the fluid chamber 53b increases and changes to the fixing pressure.

The rotation mechanism 70 will now be described.

As shown in FIG. 2 and FIG. 3, the rotation mechanism 70 principally includes a cylinder gear 71 provided in the rotary cylinder 52 and an insertion portion rotation motor 73 that is provided in a motor housing 72 that is integrally fixed to the rotation holding portion 51. The insertion portion rotation motor 73 generates a driving force that rotates the rotary cylinder 52.

The cylinder gear 71 is provided on the outer circumference of the rotary portion 52a of the rotary cylinder 52 that protrudes from the through-hole 51h of the rotation holding portion 51. The cylinder gear 71 is a cylinder side spur gear 71a that has a parallel tooth trace with respect to the central axis of the rotary cylinder 52. A motor side spur gear 74 that meshes with the cylinder side spur gear 71a is fixedly provided on a motor shaft 73a of the insertion portion rotation motor 73.

According to this configuration, the rotary cylinder 52 rotates with respect to the rotation holding portion 51 upon a rotational driving force of the insertion portion rotation motor 73 being transferred to the cylinder side spur gear 71a via the motor shaft 73a and the motor side spur gear 74. At this time, if the rotary cylinder 52 comprising the air bag 53 and the insertion portion 11 are integrated together, the insertion portion 11 is rotated accompanying rotation of the rotary cylinder 52.

Note that, to prevent the rotary cylinder 52 from performing an idle rotation with respect to the insertion portion 11, the endoscope control device 3 determines whether or not a pressure inside the fluid chamber 53b is equal to or greater than a threshold value when a twisting control signal is outputted from the button 35L or 35R. The endoscope control device 3 then controls the driving of the insertion portion rotation motor 73 based on the determined result. More specifically, when the pressure inside the fluid chamber 53b is equal to or greater than the threshold value, while the surgeon is operating the button 35L or 35R, the insertion portion rotation motor 73 is driven and the insertion portion 11 performs a twisting operation.

The cover 6 illustrated in FIG. 5 is an elastic member that is made of a resin or rubber. The hole covering portion 6a comprising the cover 6 is formed in a pipe shape having a through-hole 6d, and has a predetermined rigidity. The external diameter dimensions of the hole covering portion 6a are set to be smaller than the diameter of the insertion portion inserting hole 50a taking into account the insertability into the insertion portion inserting hole 50a. Meanwhile, the diameter dimensions of the through-hole 6d are set to be greater than the diameter of the insertion portion 11 taking into account the insertability of the insertion portion 11.

In this case, the term "predetermined rigidity" refers to a flexibility that can prevent buckling when pushing the hole covering portion 6a into the insertion portion inserting hole 50a and also convey a pressing force of the air bag 53.

The hole covering portion 6a is provided inside the insertion portion inserting hole 50a that includes the mounting/demounting hole 53a, the insertion portion introduction hole 52c, and openings 55o and 56o of the lids 55 and 56. The insertion portion 11 is inserted inside the through-hole 6d of the hole covering portion 6a that is provided inside the insertion portion introduction hole 52c.

The side surface covering portions 6b are thin-walled, circular flanges that are provided at both side sections of the hole covering portion 6a. The external diameter dimensions of the side surface covering portions 6b are set to be greater than the diameter of the proximal end face and the distal end face of the rotary cylinder 52. The side surface covering portions 6b have a flexibility that allows the side surface covering portions 6b to bend as indicated by the dashed lines in the figure. The side surface covering portions 6b are bent at the edges of the proximal end face and the distal end face of the rotary cylinder 52 such that edge portions 6e thereof are disposed at the outer peripheral face of the rotary cylinder 52.

The flexible side surface covering portions 6b are also capable of bending along the peripheral face of the hole covering portion 6a or of folding so as to be housed inside the through-hole 6d. When disposing the cover 6 inside the insertion portion inserting hole 50a of the electric bending operation device 5, the side surface covering portions 6b are bent so as to be disposed along the peripheral face of the hole covering portion 6a.

A fixing portion 6c is provided in the vicinity of the edge portion 6e of each side surface covering portion 6b. The fixing portion 6c is, for example, a belt shape. A hook and loop fastener 6f constituting a mounting/demounting portion is provided at the front surface of one end side that is fixed to the side surface covering portion 6b of the belt-shaped fixing portion 6c, and at the rear surface of the other end thereof.

In a state in which bent edge portions 6e are disposed at the outer periphery of the rotary cylinder 52, the side surface covering portions 6b cover the proximal end face and the distal end face of the rotary cylinder 52. The side surface covering portions 6b are integrally fixed to the rotary cylinder 52 by winding the belt-shaped fixing portion 6c around the edge portions 6e of the side surface covering portions 6b and matching together the hook and loop fasteners 6f.

The action of the endoscope system 1 including the electric bending operation device 5 configured as described above will now be described.

When using the electric bending operation device 5, first, the user attaches the cover 6 to the insertion portion inserting hole 50a of the electric bending operation device 5. At that time, the user bends the side surface covering portions 6b of the cover 6 to align the side surface covering portions 6b with the peripheral face of the hole covering portion 6a.

Next, the user inserts the cover 6 from an opening at one end of the insertion portion inserting hole 50a towards an opening at the other end. The user causes a folding portion (see reference numeral 6g in FIG. 5) of the side surface covering portion 6b to protrude from the opening at the other end of the insertion portion inserting hole 50a. Thereafter, the user returns the bent side surface covering portion 6b to a flange shape.

Subsequently, the user bends the respective side surface covering portions 6b to dispose the edge portion 6e at the outer peripheral face of the rotary cylinder 52. Thereafter, the user winds the belt-shaped fixing portion 6c and matches together the hook and loop fastener 6f. As a result, the cover 6 is attached in a predetermined state to the electric bending operation device 5 as shown in FIG. 6.

Next, the user inserts the insertion portion 11 of the electric bending endoscope 2 into the insertion portion inserting hole 50a from the proximal end side of the electric bending operation device 5 on which the cover 6 is mounted. More specifically, the user inserts the insertion portion 11 into the through-hole 6d of the cover 6 from the insertion portion introduction hole 52c side.

Next, when the user determines that the electric bending operation device 5 has reached a predetermined position of the flexible tube portion 16, the user connects a second supply tube 8d to the connection mouthpiece to put the device in a nitrogen gas supply state.

Thereupon, nitrogen gas is supplied into the fluid chamber 53b to expand the air bag 53. When the pressure inside the fluid chamber 53b reaches the fixing pressure, an inner face 53d of the mounting/demounting hole 53a of the air bag 53 presses the insertion portion 11 via the hole covering portion 6a of the cover 6. As a result, the rotary cylinder 52 comprising the air bag 53 and the insertion portion 11 are unified.

In this case, the surgeon inserts the insertion portion 11 into the body while, for example, observing an endoscopic image that is displayed on the screen 4a of the display device 4. At this time, the surgeon operates the lever 54 of the electric bending operation device 5 to perform operations that change the relative positions of the insertion portion 11 and the electric bending operation device 5, rotates the first knob portion 31 and the second knob portion 32 of the insertion portion operation section 30 to perform operations to bend the electric bending portion 15, and presses the buttons 35L and 35R of the twisting operation buttons 35 to perform operations to twist the insertion portion 11.

More specifically, the surgeon gradually moves the insertion portion 11 by repeatedly performing operations to insert and withdraw the insertion portion 11 in a state in which the lever 54 is disposed at the position indicated by the solid line, operations to hold the lever 54 at the position indicated by the dashed line and change the position of the electric bending operation device 5 with respect to the insertion portion 11, and operations to again insert and withdraw the insertion portion 11 in a state in which the lever 54 is disposed at the position indicated by the solid line.

Further, when releasing a hand from the lever 54 to insert the insertion portion 11 into the body, the surgeon operates the first knob portion 31 and the second knob portion 32, or the buttons 35L and 35R of the operation buttons 35. When the surgeon operates the first knob portion 31 and the second knob portion 32, the first bending portion 17 and the second bending portion 18 of the electric bending portion 15 bend in accordance with the operations of the first knob portion 31 and the second knob portion 32. When the surgeon operates the button 35L or 35R, the rotary cylinder 52 is rotated and the insertion portion 11 that is united with the rotary cylinder 52 is twisted in a direction corresponding to the button operation.

When an endoscopic image of the target site is displayed on the screen 4a of the display device 4, the surgeon carries out an inspection, insertion of a treatment instrument, a biopsy or the like. After the inspection or treatment is completed, the surgeon withdraws the insertion portion 11 from inside the body.

Thereafter, the user pulls out the insertion portion 11 from the insertion portion inserting hole 50a of the electric bending operation device 5 that is covered with the hole covering portion 6a of the cover 6. Further, after detaching the hook and loop fasteners 6f and removing the side surface covering portions 6b from the rotary cylinder 52, the user withdraws the cover 6 from the insertion portion inserting hole 50a of the electric bending operation device 5.

Thus, the configuration is one in which an air bag is provided as an insertion portion pressing member in the electric bending operation device that integrally fixes together the electric bending operation device and the insertion portion, and in which the supply of nitrogen gas to the fluid chamber of the air bag and the release of nitrogen gas from inside the air bag is performed by a lever operation. According to this configuration, a surgeon can easily switch between a state in which the insertion portion and the electric bending operation device are integrally fixed together and a state in which the electric bending operation device moves forward or rearward with respect to the insertion portion by appropriately performing a lever operation of the electric bending operation device.

The air bag having a mounting/demounting hole and a fluid chamber is provided in a hollow portion of the rotary cylinder. The air bag is expanded in a state in which the insertion portion is inserted into the mounting/demounting hole by supplying nitrogen gas to the inside of the fluid chamber. Thus, since substantially the entire circumference of the insertion portion that is disposed inside the rotary cylinder is pressed by the air bag, the insertion portion and the air bag can be integrally fixed together in a rigid condition.

The insertion portion mounting section cover comprises the hole covering portion and side surface covering portions that are provided at both side portions of the hole covering portion. When using the electric bending operation device, the cover is attached in a predetermined state, the insertion portion inserting hole is covered with the hole covering portion of the cover, and the side surface of the rotary cylinder that is the vicinity of the opening of the insertion portion inserting hole is covered with the side surface covering portion. It is therefore possible to prevent the distal end face and the proximal end face of the rotary cylinder comprising the electric bending operation device that is mounted in a condition allowing forward/rearward movement on the insertion portion, and the insertion portion inserting hole that are inserted into the body from being contaminated by the insertion portion to which dirt or the like adheres. Accordingly, by replacing only the cover after completing an endoscopic examination, the electric bending operation device can be continuously used.

Furthermore, the hole covering portion comprising the cover is made with a flexibility that enables the hole covering portion to be pushed into the insertion portion inserting hole, and the side surface covering portions are formed in a circular flange shape with thin walls having a flexibility that allows the side surface covering portions to bend. It is thus possible to bend the flexible side surface covering portions along the peripheral face of the hole covering portion, and easily dispose the hole covering portion along which the side surface covering portions are bent inside the insertion portion inserting hole of the electric bending operation device.

Note that, if evacuation of nitrogen gas from inside the fluid chamber is performed using a pump instead of using the elastic force of the air bag, it is possible to instantly perform the supply and evacuation of nitrogen gas. As a result, switching between a state in which the insertion portion can move forward/rearward and a state in which the insertion portion is fixed can be smoothly performed.

Further, in the cover 6 of the above described embodiment, the flexibility of the hole covering portion 6a and the side surface covering portion 6b are different. However, the configuration of the cover is not limited thereto, and the cover may be configured as shown in FIG. 7.

Figure 7:
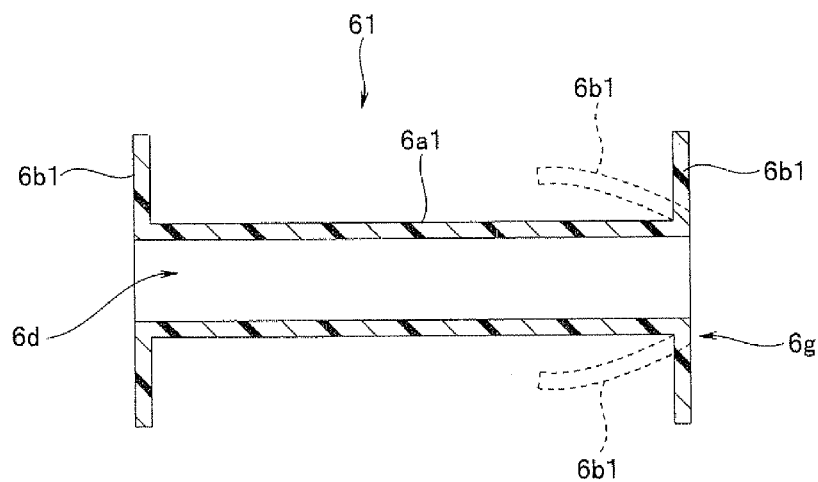
FIG. 7 is a view illustrating another configuration of the insertion portion mounting section cover.

In a cover 61 of the present embodiment that is illustrated in FIG. 7, the wall thickness of a hole covering portion 6a1 that is an elastic member and the wall thickness of a side surface covering portion 6b1 are substantially the same. When the hole covering portion 6a1 of the cover 61 is pushed inside the insertion portion inserting hole 50a, similarly to the hole covering portion 6a, buckling is prevented and the pressing force of the air bag 53 can be conveyed.

Meanwhile, regarding the side surface covering portions 6b1, the external diameter dimensions of the side surface covering portions 6b1 that are circular flanges are set to match with or to be smaller within a predetermined tolerance than the external diameter of the distal end face and the external diameter of the proximal end face of the rotary cylinder 52. The side surface covering portions 6b1 are bendable as indicated by the dashed lines and have an elastic force that returns the side surface covering portions 6b1 to their original state when an external force is released.

Figure 8:
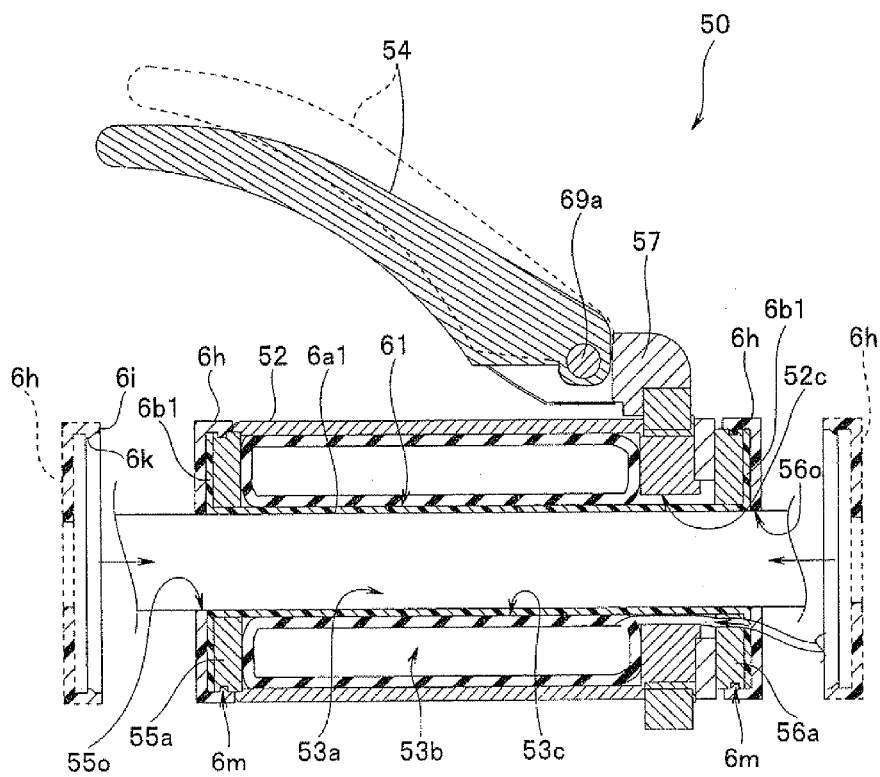
FIG. 8 is a view illustrating an electric bending operation device that includes an insertion portion mounting section cover according to another configuration.

As shown in FIG. 8, the side surface covering portions 6b1 are provided in the rotary cylinder 52 by attaching fixing disks 6h as fixing portions to lids 55a and 56a. The fixing disks 6h of the present embodiment are a flat cylindrical shape, in which a locking claw 6k that protrudes by a predetermined amount in the center direction is formed in the inner face of a peripheral wall 6i. Meanwhile, on the outer peripheral face of the lids 55a and 56a is formed a peripheral groove 6m into which the locking claw 6k is engageably inserted.

When attaching the cover 61 to the insertion portion inserting hole 50a of the electric bending operation device 5, the user bends the side surface covering portions 6b1 of the cover 61 to arrange the side surface covering portions 6b1 along the peripheral face of the hole covering portion 6a1.

Next, the user inserts the cover 61 from either opening of the insertion portion inserting hole 50a towards the other opening. The user then causes the entire folding portion 6g of the side surface covering portions 6b1 to protrude from the opening at the other end of the insertion portion inserting hole 50a.

Thereupon, the side surface covering portions 6b1 that were bent return to the flange shape due to the elastic force of the side surface covering portion 6b1. Thereafter, the user brings the side surface covering portions 6b1 at the two ends into contact with the respective lids 55a and 56a.

Subsequently, the user causes the respective locking claws 6k of the fixing disks 6h to face the lids 55a and 56a. The user then engages the locking claw 6k of each fixing disk 6h with the peripheral groove 6m of each of the lids 55a and 56a. At this time, the user pushes in the relevant fixing disk 6h against the elastic force of the side surface covering portion 6b1. As a result, the locking claw 6k is latched in the peripheral groove 6m to thereby attach the cover 61 to the electric bending operation device 5, as shown in FIG. 8.

Thus, by providing peripheral grooves in the lids and also providing locking claws that are engageably inserted into the peripheral grooves in the fixing disks, the side surface covering portions can be easily fixed to the side surfaces of the rotary cylinder.

Note that, the above-described cover 6 and cover 61 have a configuration in which flange-shaped portions of the same shape are provided at both side portions of the hole covering portion 6a. However, instead of providing flange-shaped portions of the same shape at both side portions of the hole covering portion 6a, a cover 62 may be provided that is configured as illustrated in FIG. 9.

Figure 9:
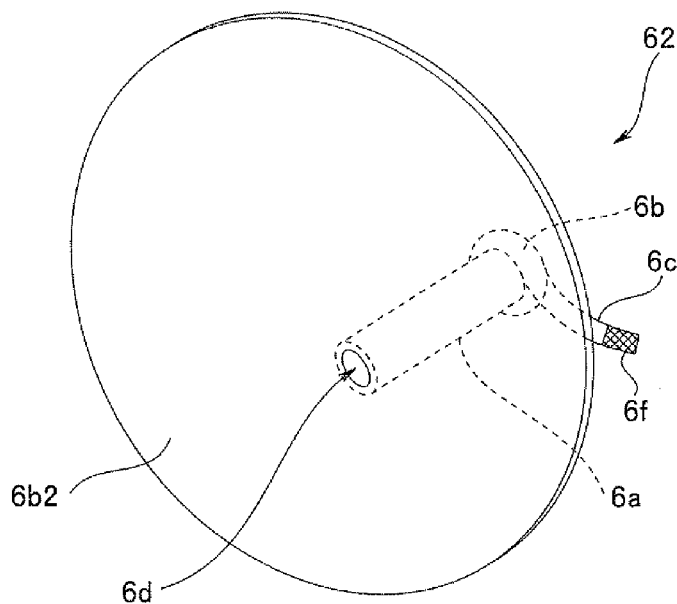
FIG. 9 is a view illustrating a different configuration of the insertion portion mounting section cover.

The cover 62 illustrated in FIG. 9 is a modification example of the cover 6. In the cover 62, a side surface covering portion 6b2 provided at one end side of the hole covering portion 6a is configured as a thin-walled sheet, which is a so-called drape. The side surface covering portion 6b2 is formed in a size that covers the electric bending operation device 5. The side surface covering portion 6b2 is folded up prior to use. The remaining configuration of the cover 62 is the same as the cover 6.

When attaching the cover 62 of the present embodiment to the insertion portion inserting hole 50a of the electric bending operation device 5, the user bends the side surface covering portion 6b of the cover 62 to dispose the side surface covering portion 6b along the peripheral face of the hole covering portion 6a.

Next, the user inserts the cover 6 from one opening of the insertion portion inserting hole 50a towards the other opening thereof. The user causes the folding portion 6g of the side surface covering portion 6b to protrude from the opening at the other end of the insertion portion inserting hole 50a. Thereafter, the user returns the bent side surface covering portion 6b to a flange shape.

Subsequently, the user unfolds the side surface covering portion 6b2 that is folded up. The user covers the side surface covering portion 6b2 over the electric bending operation device 5 while taking into account the graspability and operability of the lever 54, the graspability of the insertion portion operation section 30, and the operability of the first knob portion 31, the second knob portion 32, and the twisting operation buttons 35.

Next, after disposing the edge portion of the side surface covering portion 6b2 on a mounting portion 56c of the lid 56b, the user arranges the edge portion 6e of the side surface covering portion 6b so as to overlay the edge portion 6e on the edge portion 6e2 of the side surface covering portion 6b2.

Figure 10:
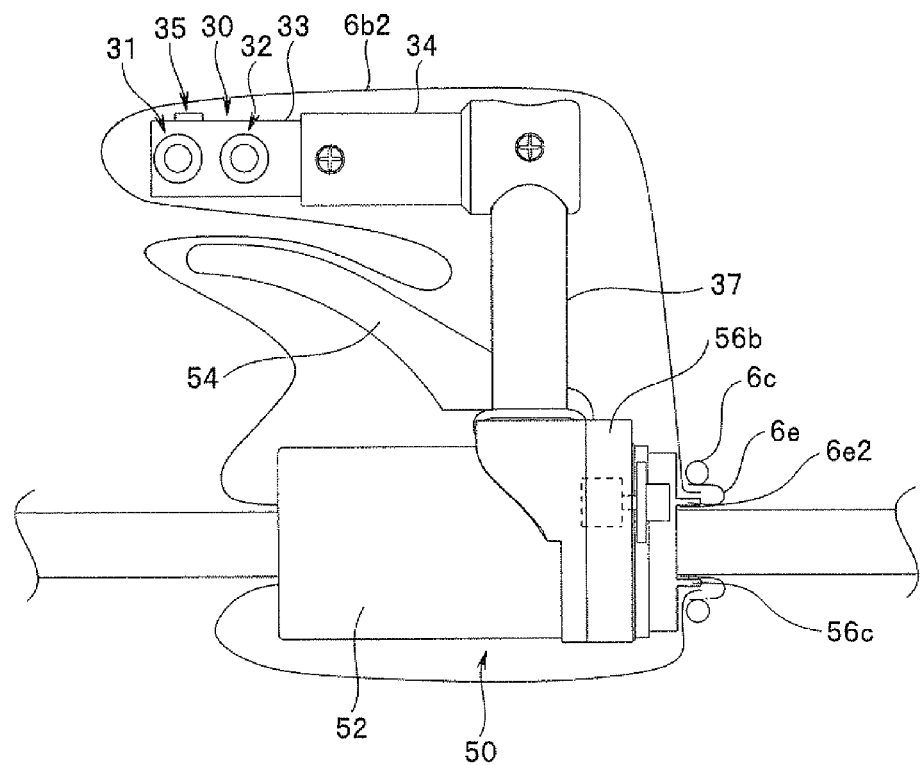
FIG. 10 is a view illustrating a state in which the electric bending operation device is covered with the insertion portion mounting section cover according to the different configuration.

Thereafter, the user winds the belt-shaped fixing portion 6c around the mounting portion and matches together the hook and loop fastener 6f. As a result, as shown in FIG. 10, the electric bending operation device 5 is covered with the side surface covering portion 6b2 of the cover 62.

Thus, by providing the cover with a side surface covering portion having the shape of a sheet that covers the entire electric bending operation device, it is possible to dispense with sterilization of the electric bending operation device after completing an endoscopic examination.

Although according to the above described embodiment the medical instrument for observation is taken to be an electric bending endoscope, the medical instrument for observation is not limited to an electric bending endoscope and, for example, may be a medical tube having an electric bending portion that is similar to that of the above described electric endoscope. The medical tube is a so-called overtube that has a channel hole through which an observation probe, an illumination probe, and a manipulator are respectively inserted. The medical tube may also be configured to include a channel hole through which an endoscope is inserted instead of the channel hole through which an observation probe and an illumination probe are respectively inserted.

Further, according to the above described embodiment, fixing of an insertion portion of an endoscope that is inserted through an insertion portion inserting hole of an electric bending operation device is performed by supplying nitrogen gas to a fluid chamber of an air bag. However, a configuration that integrally fixes an insertion portion of an endoscope that is inserted through the insertion portion inserting hole of the electric bending operation device is not limited to an air bag, and may be a configuration in which an insertion portion pressing member is a claw member as illustrated in FIG. 11 to FIG. 14.

An electric bending operation device having an insertion portion mounting mechanism with a different configuration will now be described referring to FIG. 11 to FIG. 14. Note that, members that are the same as in the above described first embodiment are denoted by the same reference numerals and a description thereof is omitted below.

Figure 11:
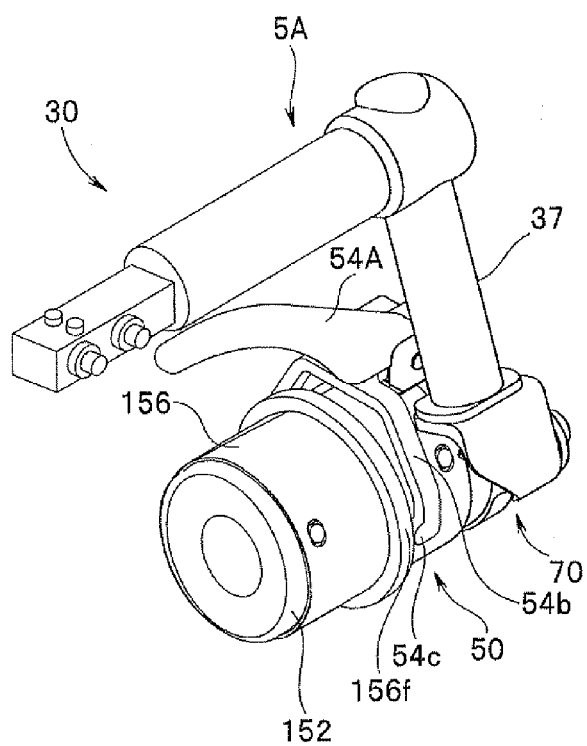
FIG. 11 is a view illustrating another configuration of the electric bending operation device.
Figure 12:
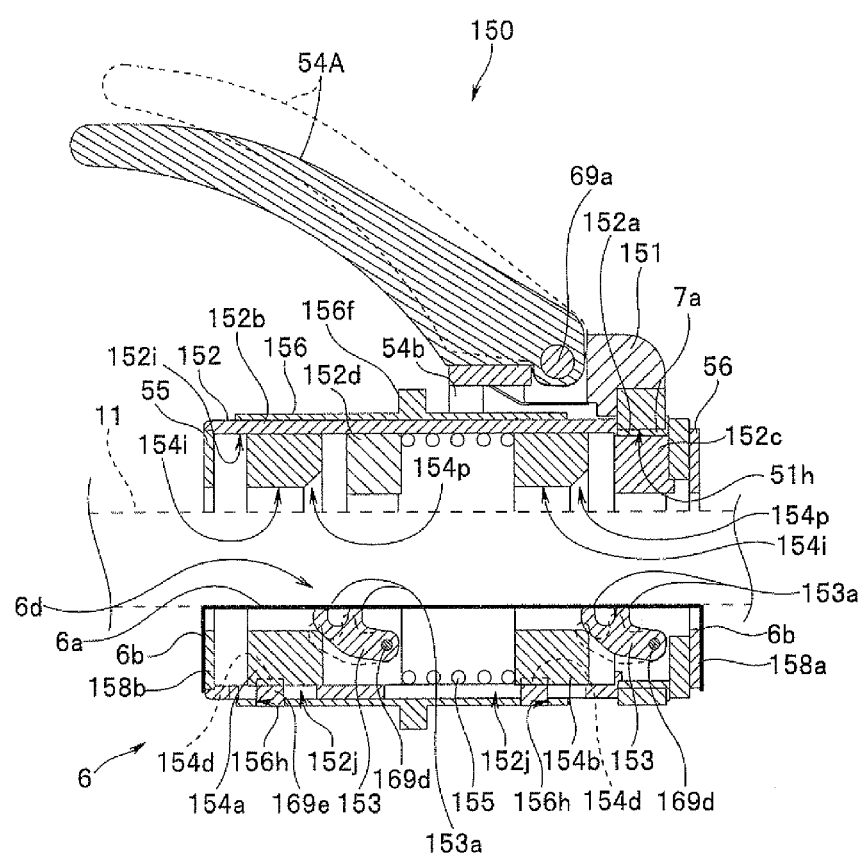
FIG. 12 is a view illustrating the configuration of an insertion portion mounting mechanism of the electric bending operation device.

As illustrated in FIG. 11 and FIG. 12, an insertion portion mounting mechanism 150 of an electric bending operation device 5A according to the present embodiment principally includes the rotation holding portion 51, a rotary cylinder 152 that also serves as the rotation mechanism 70, a plurality of claw members 153 as insertion portion pressing members, a pair of switching cylinders 154, an urging member 155, a movable cylinder 156, and a lever 54A. Reference numerals 158f and 158b denote lids. Lids 55 and 56 are fixed to the distal end face and the proximal end face of the rotary cylinder 152, respectively. In the present embodiment, the proximity switch 59 is not required.

As illustrated in FIG. 11, an inverted U-shaped arm 54b is integrally fixed to the lever 54A. Pressing portions 54c are provided at both ends of the arm 54b. When the lever 54A moves in the direction indicated by the dashed line in FIG. 12, the pressing portions 54c contact against the side surfaces on the proximal end side of an external flange 156f provided in the movable cylinder 156 to cause the movable cylinder 156 to move with respect to the rotary cylinder 152.

As shown in FIG. 12, the rotation holding portion 51 comprises the through-hole 51h. A bearing 7a is provided inside the through-hole 51h. A rotary portion 152a of the rotary cylinder 152 is rotatably disposed in the bearing 7a. The rotary cylinder 152 comprises a rotary portion 152a and a sliding portion 152b on the outer peripheral face thereof. The movable cylinder 156 configuring a switching mechanism is slidingly disposed on the outer periphery of the sliding portion 152b.

The rotary cylinder 152 has protrusions 152c and 152d that protrude in a central axis direction at a half-way portion and a proximal end side of the inner peripheral face thereof. In the present embodiment, the protrusion 152c is formed to the rotary cylinder 152. In contrast, the protrusion 152d is integrally fixed to the inner peripheral face of the rotary cylinder 152 by, for example, screwing or adhering from the outer peripheral face side.

The protrusion 152d will now be described referring to FIG. 13. Note that, the configuration of the protrusion 152c is substantially the same as the configuration of the protrusion 152d. Therefore, only the configuration of the protrusion 152d is described below, and a description of the protrusion 152c is omitted.

Figure 13:
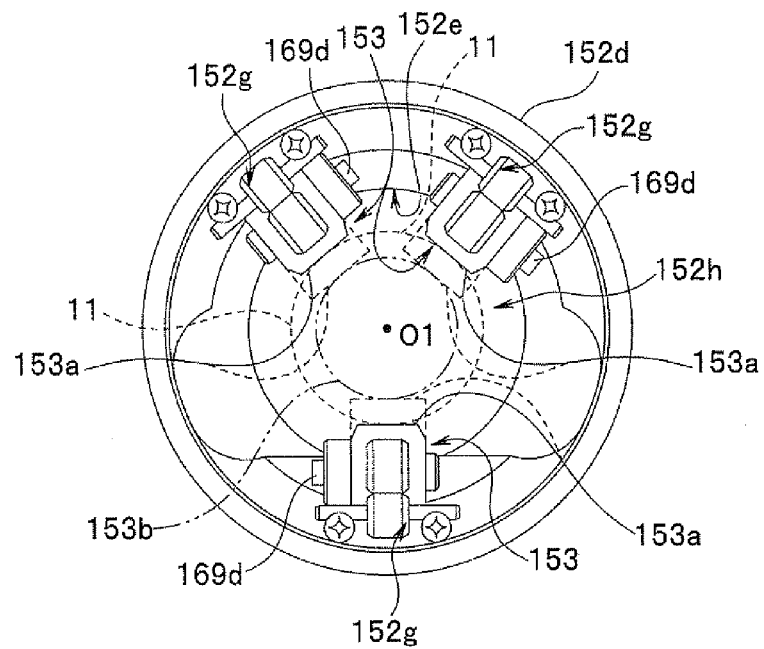
FIG. 13 is a view illustrating a protrusion and insertion portion pressing members that are provided in the protrusion.

A through-hole 152h through which the insertion portion 11 is inserted is formed as indicated by a dashed line in the protrusion 152d illustrated in FIG. 13 that is provided on the distal end side. Notched concave portions 152g for disposing the claw members 153 as insertion portion pressing members are provided at three places in the protrusion 152d. The three notched concave portions 152g are provided radially with respect to a center O1.

The claw members 153 that are disposed in the notched concave portions 152g are attached so as to rotate in the center O1 direction with pins 169d. Reference numerals 153a denote pressing portions that press the outer surface of the insertion portion 11 indicated by a dashed line to integrally fix the insertion portion 11.

The arrangement positions of the claw members 153 are set so that the longitudinal axis of the insertion portion 11 is positioned over the center O1 when the insertion portion 11 is fixed by the three pressing portions 153a.

When the claw members 153 move to a position that is furthest towards the center O1 as indicated by a chain double-dashed line, a virtual circle 153b indicated by a chain double-dashed line inscribed by the three pressing portions 153a is formed to have predetermined dimensions, a smaller diameter than the external diameter of the insertion portion 11.

Further, the pressing portions 153a are configured to withdraw to a position at which they do not contact the insertion portion 11 as indicated by the dashed line in FIG. 12 and the solid line in FIG. 13 by the urging force of an unshown spring provided to the claw members 153 in a state in which the lever 54A is grasped. When the pressing portions 153a are at the withdrawn position, the electric bending operation device 5A can be moved forward/rearward with respect to the insertion portion 11.

As shown in FIG. 12, at a position between the protrusion 152c and the protrusion 152d provided in the rotary cylinder 152 at the inner peripheral face of the rotary cylinder 152, and at a position further on the other end side than the protrusion 152d, switching cylinders 154 configuring respective switching mechanisms are slidingly disposed with respect to an inner peripheral face 152i.

Figure 14:
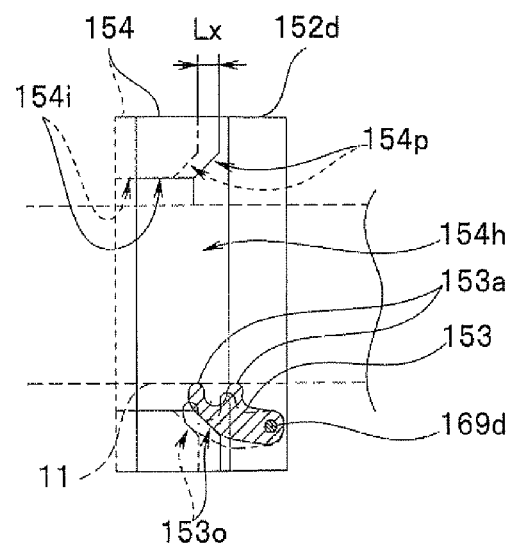
FIG. 14 is a view illustrating the relation between a switching cylinder and insertion portion pressing members.

The switching cylinders 154 are cylindrical, and have a pressing hole 154h in an axial direction that communicates an inner space 154i and the outside as shown in FIG. 14. The inner face of the pressing hole 154h is formed as a pressing face 154p. The pressing face 154p is formed as a tapered face in which the inner diameter dimensions gradually decrease to a smaller diameter towards the inner space 154i from the opening side.

Inside the pressing holes 154h, the claw members 153 are rotatably disposed on the protrusions 152c and 152d. In a state in which claw members 153 are disposed inside the pressing hole 154h, the pressing face 154p contacts against an outside surface 153o of the claw member 153 as shown by a dashed line. In this contacting state, when the switching cylinder 154 is moved, for example, by a distance Lx from the position of the dashed line by the urging member 155 as indicated by the solid line, the outside surface 153o of the claw member 153 is pressed by the pressing face 154p accompanying the movement of the switching cylinder 154. The pressing portion 153a then presses the outer surface of the insertion portion 11 as indicated by the dashed line.

As shown in FIG. 12, the switching cylinder 154 comprises a pin hole 154d in the outer peripheral face thereof. A sliding pin 169e is integrally fixed in the pin hole 154d by caulking or screwing. The length of the sliding pin 169e is set such that the sliding pin 169e protrudes to outside from the outer peripheral face of the sliding portion 152b via the long hole 152j formed in the sliding portion 152b of the rotary cylinder 152. The long hole 152j is a through-hole that communicates the inner peripheral face and outer peripheral face of the rotary cylinder 152, and is formed parallel with the longitudinal axis of the rotary cylinder 152.

The movable cylinder 156 is slidingly disposed at the sliding portion 152b of the rotary cylinder 152. The movable cylinder 156 has an external flange 156f at a predetermined position of a half-way portion of the outer peripheral face thereof. A pressing portion 54c of the arm 54b contacts against the external flange 156f. When the lever 54A is moved in the direction indicated by the dashed line in FIG. 12, the movable cylinder 156 moves to the distal end side. Two pin holes 156h in which the sliding pin 169e is disposed are formed in the movable cylinder 156. The pin holes 156h are through-holes that communicate the inner face and outer face of the movable cylinder 156.

The urging member 155 is a helical compression spring. The urging member 155 is provided between the switching cylinder 154 on the protrusion 152c side and the protrusion 152d. In the following description, of the pair of switching cylinders 154, the switching cylinder provided on the protrusion 152d side is referred to as a first switching cylinder 154a, and the switching cylinder provided on the protrusion 152c side is referred to as a second switching cylinder 154b.

The urging member 155 has an urging force that moves the two switching cylinders 154a and 154b to the proximal end side to press the insertion portion 11 with the pressing portions 153a of the claw members 153 to integrally fix the insertion portion 11. Thus, when the second switching cylinder 154b is moved by the urging force of the urging member 155, the two switching cylinders 154a and 154b move in an integrated state to the proximal end side as shown in FIG. 14.

In the electric bending operation device 5A configured as described above, the cover 6 is mounted to the insertion portion inserting hole 50a comprising the through-hole 152h of the protrusion 152c, the inner space 154i of the second switching portion 154b, the through-hole 152h of the protrusion 152d, and the inner space 154i of the switching cylinder 154a.

At that time, the user mounts the cover 6 by moving the lever 54A from the position indicated by the solid line to the position indicated by the dashed line as shown in FIG. 12, and maintaining the pressing portions 153a of the claw members 153 at the withdrawn positions indicated by dashed lines. As a result, the hole covering portion 6a of the cover 6 is disposed in the insertion portion inserting hole 50a as described above, and the side surface covering portions 6b of the cover 6 are respectively disposed via unshown fixing disks at the side surface of the lid 55 that is the distal end face of the rotary cylinder 152 and the side surface of the lid 56 comprising the proximal end face of the rotary cylinder 152.

Next, the user holds the lever 54A at the position indicated by the dashed line and inserts the insertion portion 11 of the electric bending endoscope 2 through the insertion portion inserting hole 50a of the electric bending operation device 5A to which the cover 6 is mounted. At this time, the user inserts the insertion portion 11 into the through-hole 6d of the hole covering portion 6a configuring the cover 6.

When the electric bending operation device 5A reaches a predetermined position of the flexible tube portion 16, the user releases the hand that is holding the lever 54A to release the held state. Thereupon, the two switching cylinders 154a and 154b move to the proximal end side under the urging force of the urging member 155. The pressing portions 153a of the claw members 153 then press the flexible tube portion 16 via the hole covering portion 6a such that the rotary cylinder 152 of the electric bending operation device 5A and the flexible tube portion 16 are integrally fixed together.

Thus, when pressing the insertion portion with pressing portions of claw members as insertion portion pressing members, the hole covering portion of the cover that informed with an elastic member is disposed between the insertion portion and the pressing portions of the claw members. Consequently, in comparison to a case in which a pressing portion directly presses the insertion portion, since the elastic member is provided between the pressing portions and the insertion portion, the pressing force of the pressing portion with respect to the insertion portion increases and a firm fixing force can be obtained. The other actions and advantages are the same as in the above described embodiment.

Figure 15:
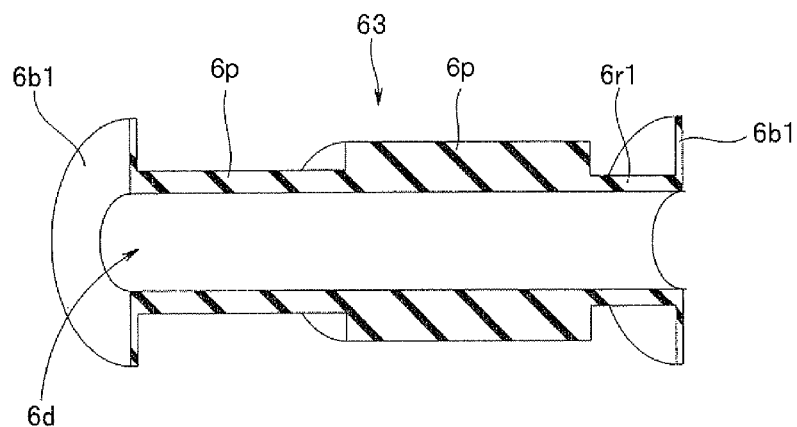
FIG. 15 is a view illustrating the configuration of an insertion portion mounting section cover that also serves as an insertion portion pressing member.

A second embodiment of the present invention will now be described referring to FIG. 15 and FIG. 16.

The cover of the present embodiment also serves as an insertion portion pressing member. A cover 63 illustrated in FIG. 15 is an elastic member and includes a clamp portion 6p, a side surface covering portion 6b1, and a short connecting portion 6r1 and a long connecting portion 6r2 that connect the clamp portion 6p and the side surface covering portion 6b1. The cover 63 includes a through-hole 6d that configures the insertion portion inserting hole 50a.

Figure 16:
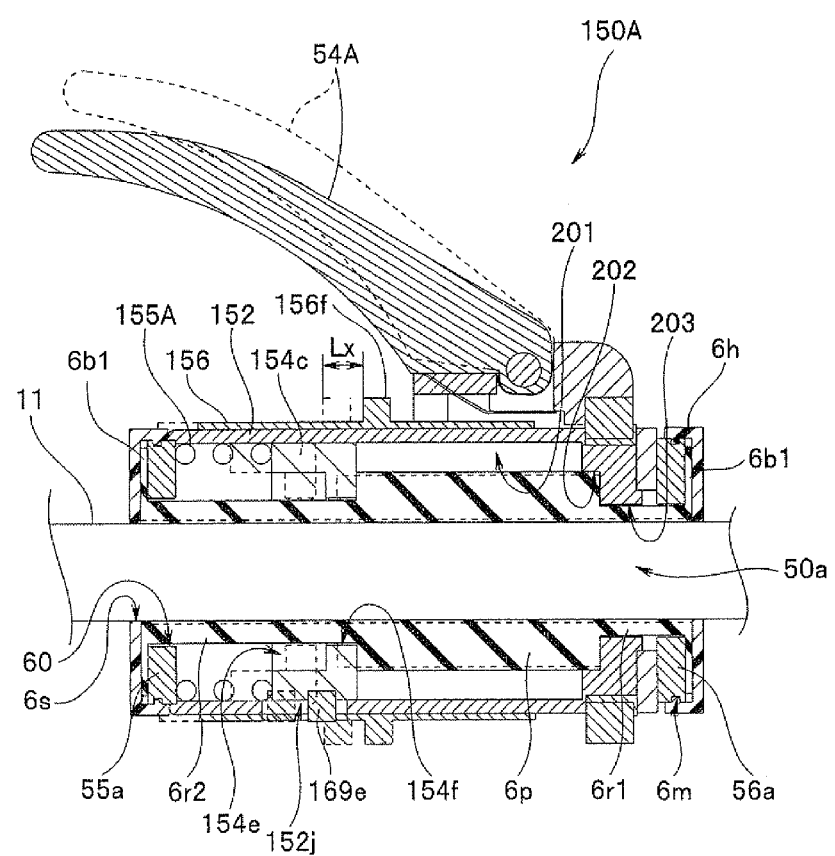
FIG. 16 is a view that illustrates an electric bending operation device according to a second embodiment, that illustrates the configuration of an insertion portion mounting mechanism provided with an insertion portion mounting section cover that also serves as an insertion portion pressing member.

As shown in FIG. 16, an insertion portion mounting mechanism 150A of the present embodiment has a configuration in which, similarly to the electric bending operation device 5A, a movable cylinder 156 and a pressing cylinder 154C move in an integrated manner with respect to the rotary cylinder 152 by operating the lever 54A.

A recess 154e that is thinned-down is formed in the pressing cylinder 154C. The recess 154e and the outside are linked by a hole 154f. The pressing cylinder 154C is urged to the proximal end side by an urging member 155A.

A rotary cylinder 152 of the present embodiment includes a hollow portion 201, a cover retaining hole 202, and an insertion portion introduction hole 203. The insertion portion introduction hole 203 is a through-hole, and communicates the hollow portion 201 comprising the cover retaining hole 202 and the outside. Reference numerals 55a and 56a denote lids. The lids 55a and 56a are respectively fixed to the distal end face and the proximal end face of the rotary cylinder 152.

The inner diameter of the insertion portion introduction hole 203 is formed with dimensions that allow the short connecting portion 6r1 of the cover 63 to freely fit therein. The end on the short connecting portion 6r1 side of the clamp portion 6p is disposed in the cover retaining hole 202. The inner diameter of the cover retaining hole 202 is set to be greater by a predetermined clearance amount with respect to the external diameter dimensions of the clamp portion 6p.

The inner diameter of the hole 154f of the pressing cylinder 154C is formed with dimensions that allow the long connecting portion 6r2 to freely fit therein. The urging member 155A is disposed between the lid 55a1 and the pressing cylinder 154C. The pressing cylinder 154C is urged in the proximal end direction of the long hole 152j by the urging force of the urging member 155A.

The remaining configuration is the same as that of the electric bending operation device 5A, and the same members are denoted by the same reference numerals and a description thereof is omitted below.

When using the electric bending operation device 5B, the user disposes the cover 63 inside the hollow portion 201 of the electric bending operation device 5B. At that time, the user bends the side surface covering portion 6b1 of the cover 63 to dispose the side surface covering portion 6b1 along the peripheral face of the short connecting portion 6r1.

Next, the user inserts the side surface covering portion 6b1 and the short connecting portion 6r1 of the cover 63 into the hollow portion 201 through an opening 6s of the fixing disk 6h and an opening 6o of the lid 55a. Thereupon, the clamp portion 6p contacts against the lid 55a.

In this case, the user moves the lever 54A to the dashed line position. Thereupon, the pressing cylinder 154C approaches the lid 55a side against the urging force of the urging member 155A. Maintaining this state, the user inserts the clamp portion 6p through the inside of the hollow portion 201 through the opening 6s of the fixing disk 6h and the opening 6o of the lid 55a.

At this time, the user pushes forward the clamp portion 6p while squashing the clamp portion 6p to insert the clamp portion 6p into the hole 154f inside the hollow portion 201. When the clamp portion 6p is inserted through the hole 154f, the user pushes forward the clamp portion 6p to pass the clamp portion 6p through the hole 154f.

Thereafter, the user disposes the end of the clamp portion 6p in the cover retaining hole 202 and inserts the end into the insertion portion introduction hole 203. Thereupon, after the side surface covering portion 6b2 and the short connecting portion 6r1 are protruded from the opening of the cover retaining hole 202, the side surface covering portion 6b1 and the short connecting portion 6r1 are disposed at the opening 6s of the fixing disk 6h.

In this case, the user takes out the side surface covering portion 6b1 from inside the opening 6s and disposes the side surface covering portion 6b2 in the lid 56a. The user then mounts the fixing disk 6h to the lid 55a. Thereafter, the user releases the held state of the lever 54A.

As a result, as shown in FIG. 16, the pressing cylinder 154C is urged in the proximal end direction by the urging force of the urging member 155A and presses the clamp portion 6p. The clamp portion 6p thereby enters a state in which the clamp portion 6p presses the insertion portion.

In the electric bending operation device 5B provided with the cover 63, the through-hole 6d of the cover 63 is the insertion portion inserting hole 50a. Therefore, in order to insert the insertion portion 11 into the insertion portion inserting hole 50a, the user holds the lever 54A at the position indicated by the dashed line shown in FIG. 12 to place the clamp portion 6p in an unloaded state. As a result, the cover 63 including the clamp portion 6p changes shape in the manner illustrated by the dashed line. That is, the through-hole 6d enters an extended state.

The user inserts the insertion portion 11 of the electric bending endoscope 2 into the through-hole 6d. When the electric bending operation device 5A reaches a predetermined position of the flexible tube portion 16, the user releases the hand that holds the lever 54A to release the held state. Thereupon, the two pressing cylinders 154C are moved to the proximal end side by the urging force of the urging member 155A and press the clamp portion 6p. Thereby, the clamp portion 6p is again compressed in the longitudinal axis direction and the inner diameter of the through-hole 6d changes to a small diameter. As a result, the clamp portion 6p presses the insertion portion 11 to integrally fix together the insertion portion 11 and the rotary cylinder 152 of the electric bending operation device 5B.

Thus, by having the cover also serve as an insertion portion pressing member, the configuration can be simplified. The other actions and advantages are the same as in the above described embodiment.

A third embodiment of the present invention will now be described referring to FIG. 17 to FIG. 20.

The electric bending operation device of the present embodiment can be mounted to an insertion portion of an endoscope in a state in which the insertion portion is inserted inside the body.

Figure 17:
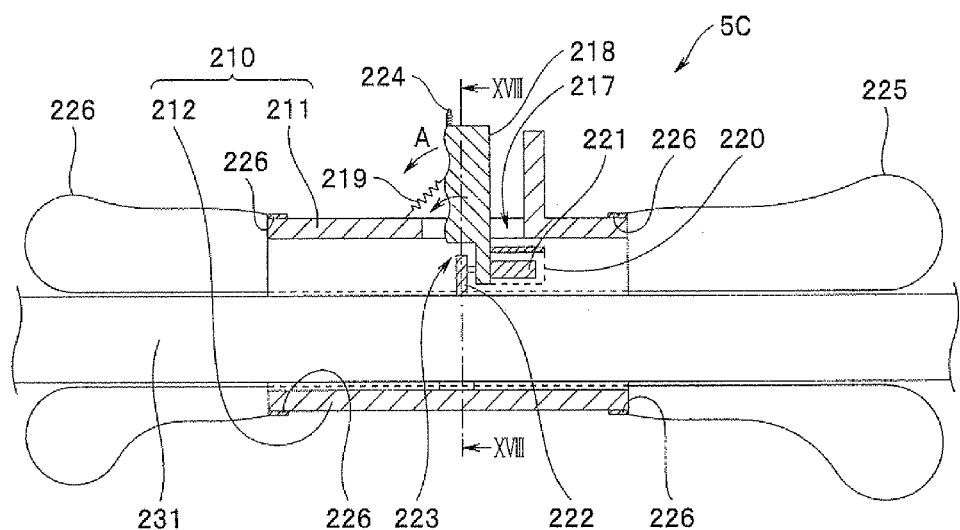
FIG. 17 is a view illustrating the configuration of an electric bending operation device as a third embodiment of the present invention.
Figure 18:
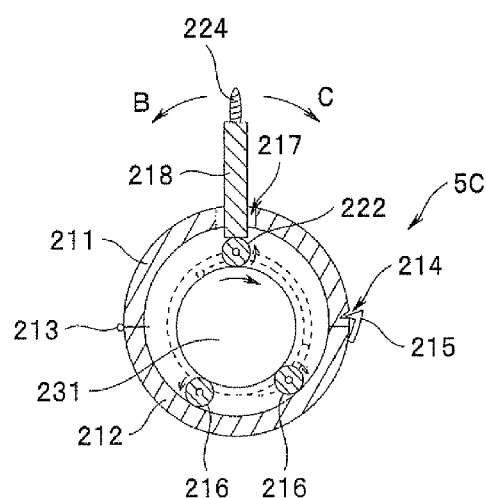
FIG. 18 is a sectional view along a line XVIII-XVIII shown in FIG. 17.

An electric bending operation device 5C illustrated in FIG. 17 and FIG. 18 includes a device main body 210 that can be divided into two pieces. The device main body 210 includes an upper structure pipe 211 and a lower structure pipe 212. The upper structure pipe 211 and the lower structure pipe 212 are each formed in a half-pipe shape, and are configured to be openable and closable by means a hinge 213. A locking groove 214 is formed in the upper structure pipe 211, and a locking claw 215 that is engageably inserted into the locking groove 214 is formed in the lower structure pipe 212.

On the inner peripheral face of the lower structure pipe 212 are arranged, for example, two driven rollers 216. A long hole 217 that is elongated in the axial direction is formed in the top face of the upper structure pipe 211. A rotation operation lever 218 is pivotally supported in a rotatable condition on the longitudinal side surface of the long hole 217. The rotation operation lever 218 is pulled and tilted in the direction of an arrow A by a spring 219. Therefore, a driving roller 222, described later, is normally in a non-contacting state with respect to the insertion portion. A motor cover 220 is provided at one end of the rotation operation lever 218.

An insertion portion rotation motor 221 is provided inside the motor cover 220. A driving roller for rotating the insertion portion (hereafter, abbreviated as "driving roller") 222 is fixedly installed on a motor shaft of the insertion portion rotation motor 221. At one end of the rotation operation lever 218 is formed a notch 223 for providing the roller 222 therein.

Reference numeral 224 denotes a rotation operation switch. The rotation operation switch 224 is configured such that when the surgeon tilts the rotation operation switch 224 in the direction of an arrow B, the insertion portion 231 rotates in a counter-clockwise direction as viewed by the surgeon, and when the surgeon tilts the rotation operation switch 224 in the direction of an arrow C, the insertion portion 231 rotates in a clockwise direction as viewed by the surgeon.

Figure 19:
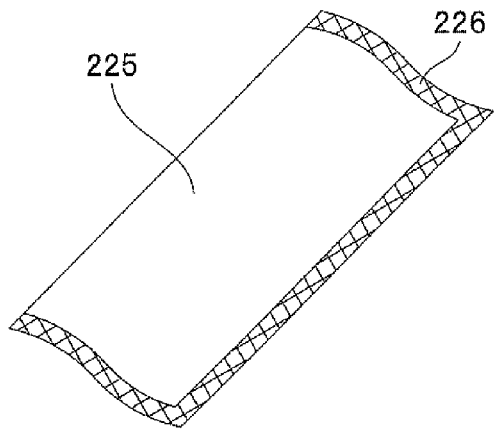
FIG. 19 is a view illustrating a drape.
Figure 20:
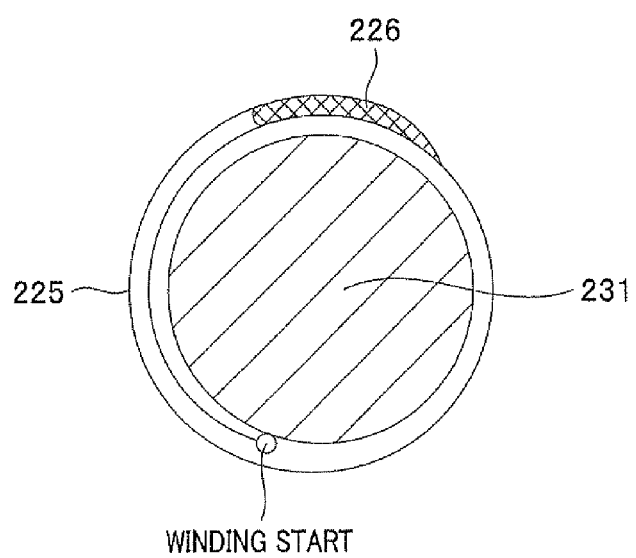
FIG. 20 is a view illustrating a drape winding section in which a drape is wound by a predetermined amount around the insertion portion.

As shown illustrated in FIG. 19, a drape 225 has a so-called rectangular shape in which a pasting margin 226 is provided at both short side ends and at one long side end. The length of the short side of the drape 225 in a state in which the long side of the drape 225 and the longitudinal axis of the insertion portion of the endoscope are parallelly disposed is a length that can be wrapped around the insertion portion 231 at least 1.5 times in the circumferential direction of the insertion portion 231 as shown in FIG. 20. The length of the long side of the drape 225 is sufficiently long with respect to the length of the device main body 210.

A case will now be described in which the electric bending operation device 5C is used, for example, in a transrectal endoscopic examination.

Figure 21:
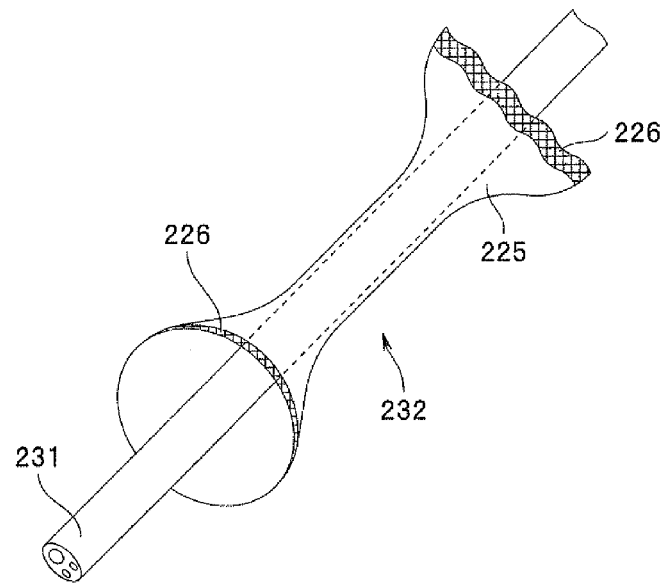
FIG. 21 is a view illustrating a drape in a state in which the drape is pasted to the insertion portion.

During the examination, when a surgeon requires the electric bending operation device 5C, the user pastes the drape 225 to a desired position of the insertion portion 231 as shown in FIG. 21 that is exposed on the side of the user's hands from the anus.

Figure 22:
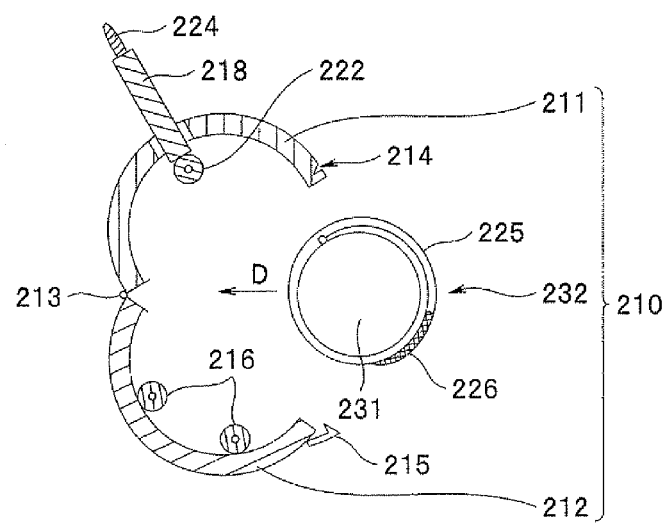
FIG. 22 is a view that describes a state in which the drape winding section is arranged in the device main body that is in an open state.

Next, the user affixes the pasting margin 226 of the drape 225 on the insertion portion 231 that is exposed on the user's hands side to the device main body 210. More specifically, as shown in FIG. 22, the user places the upper structure pipe 211 and the lower structure pipe 212 in an open state, and inserts a drape winding section 232 of the insertion portion 231 between the upper structure pipe 211 and the lower structure pipe 212.

In this case, the user aligns the drape winding section 232 so that the drape winding section 232 is disposed in a predetermined state with respect to three rollers 216, 216, and 222. The user then checks the mounting state and the positional relationship of the drape winding section 232 and the three rollers 216, 216, and 222, and engageably inserts the locking claw 215 in the locking groove 214.

As a result, the insertion portion is exposed from the device main body 210 in which the upper structure pipe 211 and the lower structure pipe 212 are united. In this case, the user folds the drape 225 at a position partway along the short side of the drape 225 and pastes and fixes the pasting margin 226 to an end of the device main body. Thus, attachment of the electric bending operation device 5C to the insertion portion 231 is completed.

Note that, the drape 225 has a sufficient length and looseness with respect to the length of the device main body 210. Therefore, even when the insertion portion 231 rotates, the drape 225 is not pulled, stretched, or torn by the influence of the insertion portion 231. Further, the rollers 216 and 222 are formed with an elastic member such as rubber.

When mounting of the electric bending operation device 5C is completed, the surgeon grasps the device main body 210 and carries out the insertion of the insertion portion 231. When rotating the insertion portion 231, the surgeon draws back the rotation operation lever 218 to the side of the surgeon's hands against the urging force of the spring 219. Thereupon, the driving roller 222 contacts against the drape winding section 232 and, further, by returning the rotation operation lever 218 to the surgeon's hand side, the rotation of the driving roller 222 is transmitted to the drape winding section 232. As a result, the insertion portion 231 performs a twisting operation.

When insertion of the insertion portion 231 as far as the target site is completed, the surgeon removes the pasting margin 226 on the short side of the drape 225 from the device main body 210, and detaches the device main body 210 from the insertion portion.

Thereafter, the surgeon grasps the insertion portion 231 from which the device main body 210 is detached and carries out the examination. If it is necessary to again mount the electric bending operation device 5C on the insertion portion 231, the user mounts the electric bending operation device 5C to the insertion portion 231 by the above described procedure.

Thus, the device main body is configured to be openable and closable. After putting the upper structure pipe and the lower structure pipe that comprise the device main body in an open state and disposing the drape insertion portion inside the device main body, the respective ends of the drape are pasted to the respective ends of the device main body. It is thus possible to mount the device main body to the insertion portion of an endoscope during use.

Further, by attaching the drape insertion portion on which the drape is mounted to the device main body, it is possible to prevent the device main body from being contaminated by dirt or the like that adheres to the insertion portion.

Furthermore, since the configuration is one in which the driving roller is brought into close contact with the insertion portion with the drape located therebetween and rotated, a driving force can be transferred to the insertion portion more effectively than a case in which the driving roller directly presses on the insertion portion.

According to the present invention, the medical operation device is described mainly taking the case of an electric bending operation device. However, the medical operation device is not limited to an electric bending operation device.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical operation device including:
    a rotary cylinder that is rotatably provided on a device main body, wherein the rotary cylinder defines a hollow portion;
    an insertion portion pressing member arranged in the hollow portion of the rotary cylinder, wherein the insertion portion pressing member includes an elastic tube element having:
    an outer surface that defines a mounting/demounting hole through which an insertion portion of a medical instrument for observation is inserted, and
    an inner surface that defines a fluid chamber, wherein the fluid chamber covers a circumference of the mounting/demounting hole; and
    an insertion portion mounting section cover that is provided in the mounting/demounting hole of the insertion portion pressing member, wherein the insertion portion mounting section cover is configured to prevent the insertion portion of the medical instrument from directly contacting the rotary cylinder and the insertion portion pressing member, and
wherein the insertion portion pressing member is configured to switch between:
    a first state in which a fluid is provided to the fluid chamber to inflate the elastic tube element to press the insertion portion mounting section cover against the insertion portion that is inserted in the mounting/demounting hole to fix the insertion portion to the rotary cylinder, and
    a second state in which the fluid is removed from the fluid chamber to deflate the elastic tube element to allow the insertion portion that is inserted in the mounting/demounting hole to move relative to the rotary cylinder,
wherein the medical operation device further includes a switch that is configured to be operated by a user to switch the insertion portion pressing member between the first state and the second state, and
wherein the rotary cylinder and the insertion portion of the medical instrument are integrally rotatable relative to the device main body when the insertion portion pressing member is configured in the second state.

* * * * *